United States Patent [19]
Commercon et al.

[11] Patent Number: 5,621,121
[45] Date of Patent: Apr. 15, 1997

[54] PROCESS FOR THE PREPARATION OF TAXANE DERIVATIVES

[75] Inventors: Alain Commercon, Vitry-sur-Seine; Eric Didier, Paris; Elie Fouque, Saint Maur des Fosses, all of France

[73] Assignee: Rhone-Poulenc Rorer S.A., Antony, France

[21] Appl. No.: 411,690

[22] PCT Filed: Oct. 4, 1993

[86] PCT No.: PCT/FR93/00969

§ 371 Date: Apr. 5, 1995

§ 102(e) Date: Apr. 5, 1995

[87] PCT Pub. No.: WO94/07879

PCT Pub. Date: Apr. 14, 1994

[30] Foreign Application Priority Data

Oct. 5, 1992 [FR] France ................... 92 11743

[51] Int. Cl.⁶ ................................................. C07D 305/14
[52] U.S. Cl. ............................................. 549/510; 549/511
[58] Field of Search ..................................... 549/510, 511

[56] References Cited

U.S. PATENT DOCUMENTS 5,319,112  6/1994  Kingston et al. ................... 549/510

FOREIGN PATENT DOCUMENTS

WO92/09589  6/1992  WIPO.

OTHER PUBLICATIONS

Voegelein et al, J. Med. Chem., vol. 34, No. 3, 1991, pp. 992–998.

Primary Examiner—Ba K. Trinh

Attorney, Agent, or Firm—Finnegan, Henderson, Farabow, Garrett & Dunner, L.L.P.

[57] ABSTRACT

This invention relates to a method of preparing taxane derivatives of formula (I) by esterification of protected baccatin III or 10-deacetylbaccatin III by means of an acid of formula (VII), elimination of protection groupings and acylation of the amine function of the side chain. The products of formula (I) have remarkable antitumor and antileukemia properties. In formulae (I) and (VII): Ar stands for aryl, R is hydrogen or acetyl, $R_1$ is a benzoyl radical or an $R_2$—O—CO— radical in which $R_2$ is alkyl, alkenyl, alkynyl, cycloalkyl, cycloalkenyl, bicycloalkyl, phenyl or heterocyclyl, $R_3$ is a trihalomethyl radical or phenyl substituted by a trihalomethyl radical, $R_4$ is a hydrogen atom or is the same as $R_1$.

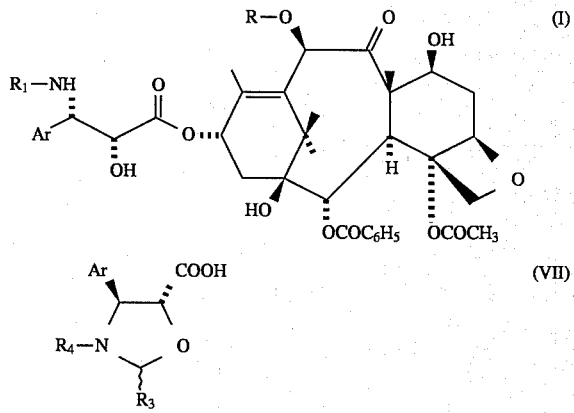

21 Claims, No Drawings

PROCESS FOR THE PREPARATION OF TAXANE DERIVATIVES

This application is a 371 of PCT/FR93/00969 filed Oct. 4, 1993.

DESCRIPTION OF THE INVENTION

The present invention relates to a new process for the preparation of taxane derivatives of general formula:

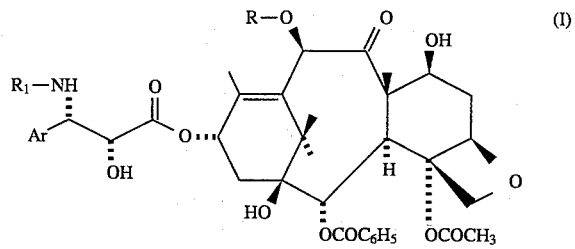

which have notable antileukaemic and antitumour properties.

In the general formula (I), R represents a hydrogen atom or an acetyl radical, $R_1$ represents a benzoyl radical or a radical $R_2$—O—CO— in which $R_2$ represents an alkyl, alkenyl, alkynyl, cycloalkyl, cycloalkenyl, bicycloalkyl, phenyl or nitrogen-containing heterocyclyl radical, and Ar represents an aryl radical.

More particularly, R represents a hydrogen atom or an acetyl radical and $R_1$ represents a benzoyl radical or a radical $R_2$—O—CO— in which $R_2$ represents:

a straight or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals optionally being substituted by one or a number of substituents chosen from the halogen atoms and the hydroxyl radical, alkyloxy radical containing I to 4 carbon atoms, dialkylamino radical, each alkyl part of which contains 1 to 4 carbon atoms, piperidino radical, morpholino radical, 1-piperazinyl radical (optionally substituted in the 4-position by an alkyl radical containing 1 to 4 carbon atoms or by a phenylalkyl radical, the alkyl part of which contains 1 to 4 carbon atoms), cycloalkyl radical containing 3 to 6 carbon atoms, cycloalkenyl radical containing 4 to 6 carbon atoms, phenyl radical, cyano radical, carboxyl radical or alkyloxycarbonyl radical, the alkyl part of which contains 1 to 4 carbon atoms, or a phenyl radical optionally substituted by one or a number of atoms or radicals chosen from the alkyl radicals containing 1 to 4 carbon atoms or the alkyloxy radicals containing 1 to 4 carbon atoms, or a saturated or unsaturated nitrogen-containing heterocyclyl radical containing 5 or 6 members, optionally substituted by one or a number of alkyl radicals containing 1 to 4 carbon atoms, it being understood that the cycloalkyl, cycloalkenyl or bicycloalkyl radicals may optionally be substituted by one or a number of alkyl radicals containing 1 to 4 carbon atoms, and Ar represents a phenyl or α- or β-naphthyl radical optionally substituted by one or a number of atoms or radicals chosen from the halogen atoms (fluorine, chlorine, bromine or iodine) and the alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano and trifluoromethyl radicals, it being understood that the alkyl radicals and the alkyl portions of the other radicals contain 1 to 4 carbon atoms, that the alkenyl and alkynyl radicals contain 3 to 8 carbon atoms and the aryl radicals are phenyl or α- or β-naphthyl radicals.

The products of general formula (I) in which R (represents a hydrogen atom or an acetyl radical, $R_1$ represents a benzoyl or t-butoxycarbonylamino radical and Ar represents a phenyl radical are very particularly anvantageous.

The products of general formula (I) in which $R_1$ represents a benzoyl radical correspond to taxol and to 10-deacetyltaxol and the products of general formula (I) in which $R_1$ represents a t-butoxycarbonyl radical correspond to those which form the subject of European Patent EP 0,253,738.

According to the process which is described in International Application PCT WO 92/09589, the derivatives of general formula (I) can be obtained by:

condensation of a derivative of the oxazolidine of general formula:

in which Ar is defined as above, Boc represents the t-butoxycarbonyl radical and $R'_2$ and $R'_3$, which are identical or different, represent an alkyl radical containing 1 to 4 carbon atoms, optionally substituted by one or a number of aryl radicals, or an aryl radical, or else $R'_2$ and $R'_3$ form, together with the carbon atom to which they are bonded, a ring having from 4 to 7 members, with the protected baccatin IIT or 10-deacetylbaccatin (III of general formula:

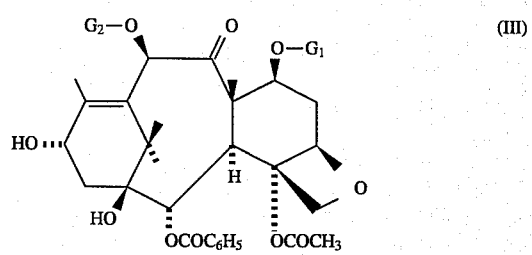

in which $G_1$ represents a protective group of the hydroxyl functional group and G, represents an acetyl radical or a protective group of the hydroxyl functional group, to produce a product of general formula:

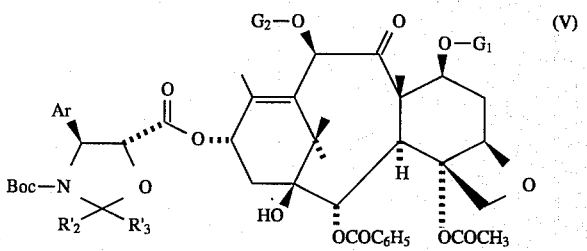

in which Ar, $R'_2$, $R'_3$, $G_1$, $G_2$ and Boc are defined as above, treatment in acidic medium of the product of general formula (IV) under conditions which are without effect on $G_1$ and $G_2$ to produce the product of general formula:

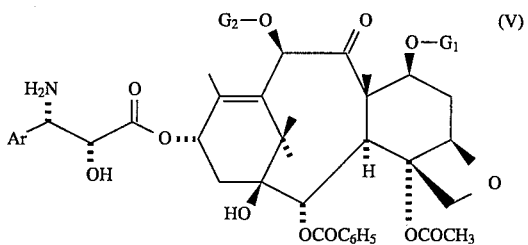

in which Ar, $G_1$ and $G_2$ are as defined above, treatment of the product of general formula (V) with a reagent suitable for introducing a radical $R_1$, that is to say a benzoyl or $R_2$—O—CO— radical, to produce a product of general formula:

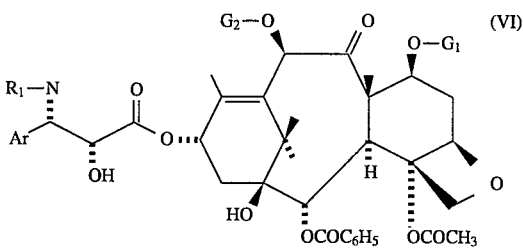

in which Ar, $R_1$, $G_1$ and $G_2$ are defined as above, and replacement of the protective groups $G_1$ and $G_2$ of the product of general formula (VI) by hydrogen atoms to produce the product of general formula (I).

It has now been found, and it is this which forms the subject of the present invention, that the products of general formula (I) can be obtained:

1) by esterifying the protected baccatin III or 10-deacetyl-baccatin III of general formula (III), in which $G_1$ and optionally $G_2$ represent a protective group of the hydroxyl functional group, using an acid of general formula:

in which Ar is defined as above, $R_3$ represents a trihalomethyl, preferably trichloromethyl, radical or a phenyl radical substituted by a trihalomethyl, preferably trichloromethyl, radical, or of a derivative of this acid, and $R_4$ represents a hydrogen atom or is identical to $R_1$ defined as above, to produce a product of general formula:

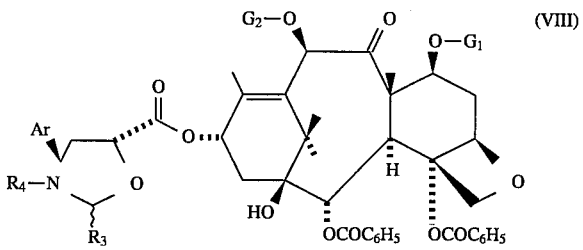

in which Ar, $R_3$, $R_4$, $G_1$ and $G_2$ are defined as above, 2) by replacing protective groups of the hydroxyl and amino functional groups of the product of general formula (VIII) by hydrogen atoms to produce the product of formula:

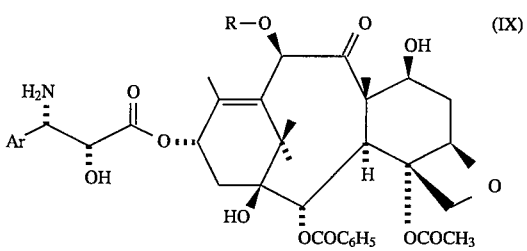

3) by treating the product obtained of general formula (IX) with a reagent which makes it possible to introduce a substituent $R_1$ onto the amino functional group to produce a product of general formula (I).

According to the present invention, eeterification of the protected baccatin III or of the protected 10-deacetylbaccatin III of general formula (III) with an acid of general formula (VII), in which $R_4$ preferably represents a hydrogen atom, can be carried out in the presence of a condensation agent such as a diimide, such as dicyclohexylcarbodiimide, or a reactive carbonate such as di-2-pyridyl ketone and of an activating agent such as an aminopyridine, such as 4-dimethylaminopyridine or 4-pyrrolidinopyridine, the reaction being carried out in an organic solvent chosen from ethers such as tetrahydrofuran, diisopropyl ether, methyl t-butyl ether or dioxane, ketones such as methyl isobutyl ketone, esters such as ethyl acetate, isopropyl acetate or n-butyl acetate, nitriles such as acetonitrile, aliphatic hydrocarbons such as pentane, hexane or heptane, halogenated aliphatic hydrocarbons such as dichloromethane or 1,2-dichloroethane and aromatic hydrocarbons such as benzene, toluene, xylenes, ethylbenzene, isopropylbenzene or chlorobenzene, at a temperature between 10° and 90° C. It is particularly advantageous to carry out the esterification in an aromatic hydrocarbon at a temperature in the region of 20° C.

The esterification can also be carried out by using the acid of general formula (VII) in the anhydride form of general formula:

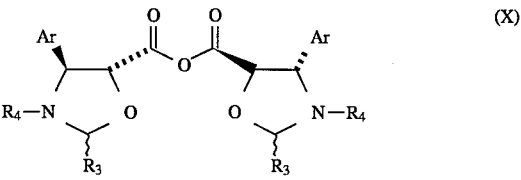

in which Ar, $R_3$ and $R_4$ are defined as above, in the presence of an activating agent such as an aminopyridine, such as 4-dimethylaminopyridine or 4-pyrrolidinopyridine, the reaction being carried out in an organic solvent chosen from ethers such as tetrahydrofuran, diisopropyl ether, methyl t-butyl ether or dioxane, ketones such as methyl isobutyl ketone, esters such as ethyl acetate, isopropyl acetate or n-butyl acetate, nitriles such as acetonitrile, aliphatic hydrocarbons such as pentane, hexane or heptane, halogenated aliphatic hydrocarbons such as dichloromethane or 1,2-dichloroethane and aromatic hydrocarbons such as benzene, toluene, xylenes, ethylbenzene, isopropylbenzene or chlorobenzene, at a temperature between 0° and 90° C.

The esterification can also be carried out by using the acid of general formula (VII) in the halide form or mixed anhydride form of general formula:

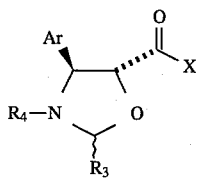

(XI)

in which Ar, $R_3$ and $R_4$ are defined as above, $R_4$ preferably representing a hydrogen atom, and X represents a halogen atom or an acyloxy or aroyloxy radical, optionally prepared in situ, in the presence of a base which is preferably a nitrogenous organic base such as a tertiary aliphatic amine, a pyridine or an aminopyridine such as 4-dimethylaminopyridine or 4-pyrrolidinopyridine, the reaction being carried out in an inert organic solvent chosen from ethers such as tetrahydrofuran, diisopropyl ether, methyl t-butyl ether or dioxane, ketones such as methyl t-butyl ketone, esters such as ethyl acetate, isopropyl acetate or n-butyl acetate, nitriles such as acetonitrile, aliphatic hydrocarbons such as pentane, hexane or heptane, halogenated aliphatic hydrocarbons such as dichloromethane or 1,2-dichloroethane and aromatic hydrocarbons such as benzene, toluene, xylenes, ethylbenzene, isopropylbenzene or chlorobenzene, at a temperature between 10° and 80° C., preferably in the region of 20° C.

Preferably, an activated derivative of general formula (XI) is used in which X represents a halogen atom or an acyloxy radical containing 1 to 5 carbon atoms or an aryloxy radical in which the aryl part is a phenyl radical optionally substituted by 1 to 5 atoms or radicals, which are identical or different, chosen from halogen atoms (chlorine, bromine) and nitro, methyl or methoxy radicals.

Replacement by hydrogen atoms of the protective groups of the hydroxyl and amino functional groups of the product of general formula (VIII), in which, preferably, $G_1$ and optionally $G_2$ represent a 2,2,2-trichloroethoxycarbonyl or 2-(2-(trichloromethyl)propoxy)carbonyl radical, is generally carried out by treatment with zinc, optionally in combination with copper, in the presence of acetic acid at a temperature between 20° and 60° C. or using an inorganic or organic acid, such as hydrochloric acid or acetic acid in solution in an aliphatic alcohol containing 1 to 3 carbon atoms or in an aliphatic ester (ethyl acetate, isopropyl acetate, n-butyl acetate) in the presence of zinc, optionally in combination with copper.

Replacement of the protective groups of the product of general formula (VIII) by hydrogen atoms can also be carried out by electrolytic reduction.

The introduction of a substituent $R_1$ onto the amino functional group of the product of general formula (IX) is carried out by reacting with benzoyl chloride or with the reactive derivative of general formula:

$$R_2\text{—O—CO—Y} \qquad (XII)$$

in which $R_2$ is defined as above and Y represents a halogen atom or a residue —O—$R_2$ or —O—CO—$R_2$, the reaction being carried out in an organic solvent such as an aliphatic ester, such as ethyl acetate, or an alcohol, such as methanol, ethanol, isopropanol or n-butanol, or a halogenated aliphatic hydrocarbon, such as dichloromethane, in the presence of an inorganic or organic base, such as sodium bicarbonate. Generally, the reaction is carried out at a temperature between 0° and 50° C., preferably in the region of 20° C.

The acid of general formula (VII) can be obtained by saponification in basic medium of the ester of general formula:

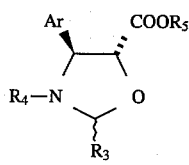

(XIII)

in which Ar, $R_1$ and $R_4$ are defined as above and $R_5$ represents an alkyl radical containing 1 to 4 carbon atoms optionally substituted by a phenyl radical.

Generally, the saponification is carried out using an inorganic base such as an alkali metal hydroxide (lithium, potassium, sodium) or an alkali metal carbonate or bicarbonate (sodium bicarbonate, potassium carbonate or potassium bicarbonate) in aqueous/alcohol medium, such as a methanol/water mixture, at a temperature between 10° and 40° C., preferably in the region of 20° C.

The ester of general formula (XIII) can be obtained by reacting an aldehyde of general formula:

$$R_3\text{—CHO} \qquad (XIV)$$

in which $R_3$ is defined as above, optionally in the form of a dialkyl acetal, with a phenylisoserine derivative of general formula:

(XV)

in which Ar, $R_4$ and $R_5$ are defined as above, in the racemic form or, preferably, in the 2R,3S form, the reaction being carried out in an inert organic solvent in the presence of a strong inorganic acid, such as sulphuric acid, or organic acid, such as p-toluenesulphonic acid, optionally in the pyridinium salt form, at a temperature between 0° C. and the boiling temperature of the reaction mixture. Solvents which are particularly well suited are aromatic hydrocarbons.

The product of general formula (XV) can be prepared under the conditions described or by adaptation of the methods described in International Application PCT WO 92/09589.

The anhydride of general formula (X) can be obtained by reacting a dehydrating agent, such as dicyclohexylcarbodiimide, with the acid of general formula (VII), the reaction being carried out in an organic solvent chosen from ethers, such as tetrahydrofuran, diisopropyl ether, methyl t-butyl ether or dioxane, ketones such as methyl isobutyl ketone, esters such as ethyl acetate, isopropyl acetate or n-butyl acetate, nitriles such as acetonitrile, aliphatic hydrocarbons such as pentane, hexane or heptane, halogenated aliphatic hydrocarbons such as dichloromethane or 1,2-dichloroethane, and aromatic hydrocarbons such as benzene, toluene, xylenes, ethylbenzene, isopropylbenzene or chlorobenzene, at a temperature between 0° and 30° C.

The activated acid of general formula (XI) can be obtained by reacting a sulphuryl halide, preferably the chloride, or a product of general formula:

$$R_4\text{—CO—Z} \qquad (XVI)$$

in which $R_6$ represents an alkyl radical containing 1 to 4 carbon atoms or a phenyl radical optionally substituted by 1 to 5 atoms or radicals, which are identical or different, chosen from halogen atoms and nitro, methyl or methoxy radicals and Z represents a halogen atom, preferably a chlorine atom, with an acid of general formula (VII), the reaction being carried out in a suitable organic solvent, such as tetrahydrofuran, in the presence of an organic base, such as a tertiary amine such as triethylamine, at a temperature between 0° and 30° C.

EXAMPLES

The following example illustrates the present invention.

Example 0.21 g of dicyclohexylcarbodiimide is added, at a temperature in the region of 20° C., to a solution of 0.33 g of (4S,5R)-4-phenyl-2-trichloromethyl-1,3-oxazolidine-5-carboxylic acid, of 0.49 g of 4-acetoxy-2α-benzoyloxy-5β, 20-epoxy-1,13α-dihydroxy-9-oxo-7α,10β-bis (2,2,2-trichloroethoxy) carbonyloxy-11-taxene and of 0.013 g of 4-dimethylaminopyridine in 2.77 cm$^3$ of anhydrous toluene. The solution is stirred at 25° C. for 2–3 hours and the dicyclohexylurea formed is then filtered through a sintered glass. The precipitate is rinsed with 20 cm$^3$ of ethyl acetate and the organic phase is washed successively with 20 cm$^3$ of a molar aqueous hydrochloric acid solution, 20 cm$^3$ of a saturated aqueous sodium bicarbonate solution and 10 cm$^3$ of a saturated aqueous sodium chloride solution. The organic phase is dried over sodium sulphate and concentrated to dryness under reduced pressure to give 0.78 g of crude product which is purified by filtration through 20 g of silica gel, the eluent being an ethyl acetate/n-hexane (v/v=4/6) mixture. After concentrating to dryness under reduced pressure, there is obtained 0.70 g of 4-acetoxy-2α-benzoyloxy-5β,20-epoxy-1-hydroxy-9-oxo-7β,10β-bis (2,2,2trichloroethoxy) carbonyloxy-11-taxene-13α-yl (4R, 5S)-4-phenyl-2-trichloromethyl-1,3-oxazolidine-5-carboxylate in the form of a mixture of two diastereoisomers whose characteristics are the following:

infrared spectrum (as a pellet with KBr): main characteristic absorption bands at 1760, 1730, 1600, 1585, 1490, 1450, 1250, 1065, 980, 810, 760, 725–700 cm$^{-1}$ proton nuclear magnetic resonance spectrum (400 MHz; CDCl$_3$; chemical shifts δ in ppm; coupling constants J in Hz) (mixture of diastereoisomers in the proportions 70/30); 1.15 to 1.30 (mt, 6H), 1.84 (s, 1H), 1.86 (s, 1H), 2.07 (s, 1H), 2.00 to 2.10 (mt, 1H), 2.15 (s, 1H), 2.10 to 2.30 (mt, 2H), 2.55 to 2.70 (mt, 1H), 3.20 (large unresolved peak, 1H), 3.32 (large unresolved peak, 1H), 3.87 (d, J=7, 1H), 3.94 (d, J=7, 1H), 4.10 (d, J=S, 1H), 4.13 (d, J=8, 1H), 4.27 (d, J=8, 1H), 4.30 (d, J=8, 1H), 4.58 (d, J=7.5, 1H), 4.61 (d, J=12, 1H), 4.63 (d, J=12, 1H), 4.70 (d, J=8, 1H), 4.80 (AB, 2H), 4.80 (mt, 1H), 4.85 to 5.00 (mt, 2H), 5.13 (d, J=7.5, 1H), 5.53 (broad s, 1H), 5.56 (dd, J=11 and 7, 1H), 5.60 (dd, J=11 and 7, 1H), 5.66 (d, J=7, 1H), 5.68 (d, j=7, 1H), 6.20 to 6.35 (mt, 1H), 6.24 (s, 1H), 6.27 (s, 1H), 7.30 to 7.50 (mt, 3H), 7.30 to 7.70 (mt, 3H), 7.60 (d, 2H), 8.03 (d, J=7.5, 2H).

0.27 g of zinc powder and 1.07 cm$^3$ of acetic acid are added to a solution of 0.50 g of 4-acetoxy-2α-benzoyoxy-5β, 20-epoxy-1-hydroxy-9-oxo -7β, 10β-bis (2,2,2-trichloroethoxy) carbonyloxy-11-taxen-13α-yl (4S, 5R)-4-phenyl-2-trichloromethyl-1,3-oxazol idine-5 carboxylate in 5 cm$^3$ of ethyl acetate. The solution is stirred at a temperature in the region of 20° C. for 15 hours and then filtered through a sintered glass. The precipitate is washed with ethyl acetate (20 cm$^3$) and the organic phase is washed successively with water (15 cm$^3$) and with a saturated aqueous sodium bicarbonate solution (2 times 15 cm$^3$) and then dried over sodium sulphate. The solution is then concentrated to dryness under reduced pressure at 35° C. to give 0.33 g of an amorphous solid. Quantitative determination by high performance liquid chromatography shows that 4-acetoxy-2α-benzoyloxy-5β, 20-epoxy-1,7β, 10β-trihydroxy-9-oxo-11-taxen-13α-yl (2R, 3S)-3-amino -3-phenyl-2-hydroxypropionate, assaying at 50%, is obtained with a yield of 65%.

The characteristics of the product obtained are the following:

proton nuclear magnetic resonance spectrum (400 MHz; d$_6$-DMSO; chemical shifts δ in ppm; coupling constants J in Hz): 0.99 (s, 3H), 1.03 (s, 3H), 1.53 (s, 3H), 1.65 (mt, 1H), 1.75 (s, 3H), 1.70 to 1.90 (mt, 2H), 2.12 (s, 3H), 2.28 (mt, 1H), 3.65 (d, J=7, 1H), 4.02 (AB, J=8, 2H), 4.00 to 4.15 (mt, 3H), 4.56 (s, 1H), 4.90 (broad d, J=10, 1H), 4.99 (broad s, 1H), 5.05 (large unresolved peak, 1H), 5.10 (s, 1H), 5.42 (d, J=7, 1H), 5.88 (t, J=9, 1H), 7.15 to 7.45 (mt, 5H), 7.65 (t, J=7.5, 2H), 7.73 (t, J-7.5, 1H), 7.98 (d, J=7.5, 2H).

0.11 g of di-tert-butyl dicarbonate is added to a solution of 0.30 g of crude 4-acetoxy-2α-benzoyloxy-5β, 20-epoxy-1,7β, 10β-trihydroxy-9-oxo-11-taxen-13β-yl (2R, 3S)-3-amino-3-phenyl-2-hydroxypropionate, obtained above, in 5 cm$^3$ of methanol. The reaction mixture is stirred at a temperature in the region of 20° C. for 15 hours, and then 20 cm$^3$ of water are added. The solution is extracted three times with 15 cm$^3$ of methylene chloride. The combined organic phases are dried over sodium sulphate and then concentrated to dryness under reduced pressure. 0.395 g of crude product is thus obtained. Quantitative determination by high performance liquid chromatography shows that the 4-acetoxy-2α-benzoyloxy-5β,20-epoxy-1,7β,10β-trihydroxy-9-oxo-11-taxen-13α-yl (2R,3S)-3-(tert-butoxycarbonylamino)-3-phenyl-2-hydroxypropionate yield is 70%.

(4S,SR)-4-Phenyl-2-trichloromethyl-1,3-oxazolidine-5-carboxylic acid can be prepared in the following way:

A solution of 3.0 g of methyl (2R,3S)-3-(tert-butoxycarbonylamino)-2-hydroxy-3-phenylpropionate, of 5 cm$^3$ of chloral and of 0.05 g of pyridinium p-toluenesulphonate in 40 cm$^3$ of anhydrous toluene is heated at reflux with distillation of the solvent. 15 cm$^3$ of solvent are distilled and then 5 cm$^3$ of chloral and 0.05 g of pyridinium p-toluenesulphonate are added. 20 cm$^3$ of solvent are distilled and then 5 cm$^3$ of chloral as well as 30 cm$^3$ of anhydrous toluene are added. 25 cm$^3$ of solvent are distilled and 5 cm$^3$ of chloral and 35 cm$^3$ of anhydrous toluene are added. 25 cm$^3$ of solvent are distilled and then the solution is cooled to a temperature in the region of 20° C. The organic solution is washed with water (2 times 50 cm$^3$), dried over sodium sulphate and concentrated to dryness under reduced pressure at approximately 50° C. The residue obtained is purified by liquid chromatography on silica gel, the eluent being an ethyl acetate/cyclohexane (⅓ by volume) mixture. There are thus obtained, with a yield of 91%, 3.0 g of (4S,5R)-5-methoxycarbonyl-4-phenyl-2-trichloromethyl-1,3-oxazolidine whose characteristics are the following:

infrared spectrum (CCl$_4$): characteristic absorption bands at 3400, 3100, 3075, 3040, 2960, 1755, 1605, 1590, 1495, 1460, 1440, 1205 and 700 cm$^{-1}$ proton nuclear magnetic resonance spectrum (200 MHz; d$_6$-DMSO; chemical shifts δ in ppm; coupling constants J in Hz) (mixture of diastereoisomers in the proportion 65/35): 3.62 (s, 3H), 3.72 (s, 3H), 4.50 (d, J=7.5 1H), 4.50 to 4.70 (large unresolved peak, 1H), 4.62 (broad d, J=7.5, 1H), 4.66 (limit AB, 2H), 5.22 (large unresolved peak, 1H), 5.40 (s, 1H), 5.43 (s, 1H), 7.30 to 7.70 (mt, 5H).

A solution of 1.49 g of lithium hydroxide monohydrate in 40 cm$^3$ of water is added to a solution of 10.48 g of (4S, 5R)-5-methoxycarbonyl-4-phenyl-2-trichloromethyl-1,3- oxazolidine in 120 cm³ of methanol. The solution is stirred at a temperature in the region of 20° C. for 1 hour and the methanol is then evaporated under reduced pressure at 40° C. The residual aqueous phase is then acidified with 35 cm³ of 1M aqueous hydrochloric acid solution. 80 cm³ of ethyl acetate are then added with vigorous stirring. The aqueous phase is withdrawn and extracted again with 80 cm³ of ethyl acetate. The organic phases are combined, dried over sodium sulphate and concentrated to dryness under reduced pressure. The residue obtained is dried overnight at reduced pressure at a temperature in the region of 20° C. There are thus obtained 10.03 g of (4S,5R)-4-phenyl-2-trichloromethyl-1,3-oxazolidine-5-carboxylic acid whose characteristics are the following:

infrared spectrum (CHBr₃): characteristic bands at 3380, 3325–2240, 1730, 1600, 1495, 1455, 810 and 760 cm⁻¹ proton nuclear magnetic resonance spectrum (200 MHz; d₆-DMSO; chemical shifts δ in ppm; coupling constants J in Hz): 4.39 (d, J=7.5, 1H), 4.40 to 4.70 (mt, 2H), 5.13 (mt, 1H), 5.37 (s, 1H), 5.41 (s, 1H), 7.10 to 7.60 (mt, 5H).

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the preparation of taxane derivatives of formula:

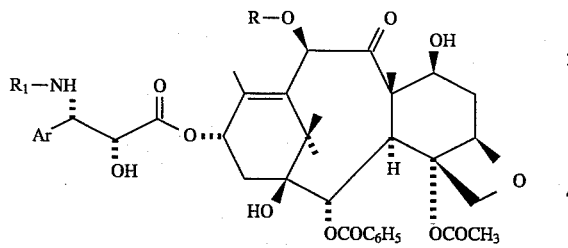

in which:

R represents a hydrogen atom or an acetyl radical, R₁ represents a benzoyl radical or a radical R₂—O—CO- in which R₂ represents:

a straight or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals optionally being substituted by at least one substituent selected from the halogen atoms and the hydroxyl radical, alkyloxy radical containing 1 to 4 carbon atoms, dialkylamino radical, each alkyl part of which contains 1 to 4 carbon atoms, piperidino radical, morpholino radical, 1-piperazinyl radical (optionally substituted in the 4-position by an alkyl radical containing 1 to 4 carbon atoms or by a phenylalkyl radical, the alkyl part of which contains 1 to 4 carbon atoms), cycloalkyl radical containing 3 to 6 carbon atoms, cycloalkenyl radical containing 4 to 6 carbon atoms, phenyl radical, cyano radical, carboxyl radical or alkyloxycarbonyl radical, the alkyl part of which contains 1 to 4 carbon atoms, or a phenyl radical optionally substituted by at least one atom or radical selected from the alkyl radicals containing 1 to 4 carbon atoms or the alkyloxy radicals containing 1 to 4 carbon atoms, or a saturated or unsaturated nitrogen-containing heterocyclyl radical containing 5 or 6 members, optionally substituted by at least one alkyl radical containing 1 to 4 carbon atoms, the cycloalkyl, cycloalkenyl or bicycloalkyl radicals optionally is substituted by at least one alkyl radical containing 1 to 4 carbon atoms, and Ar represents a phenyl or α- or β-naphthyl radical optionally substituted by at least one atom or radical selected from the halogen atoms including fluorine, chlorine, bromine or iodine and the alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano and trifluoromethyl radicals, the alkyl radicals and the alkyl portions of the other radicals contain 1 to 4 carbon atoms, the alkenyl and alkynyl radicals contain 3 to 8 carbon atoms and the aryl radicals are phenyl or α- or β-naphthyl radicals, comprising 1) esterifying a derivative of the protected baccatin III or of the protected 10-deacetylbaccatin III of formula:

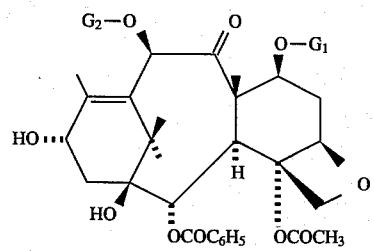

in which G₁ and optionally G₂ represent a protective group of the hydroxyl functional group, an acid of formula:

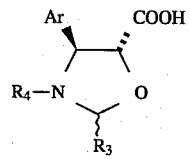

in which Ar is defined as above, R₃ represents a trihalomethyl 2) radical or phenyl radical substituted by a trihalomethyl radical, R₄ represents a hydrogen atom or is identical to R₁ defined above, or of a derivative of this acid, to produce a product of formula:

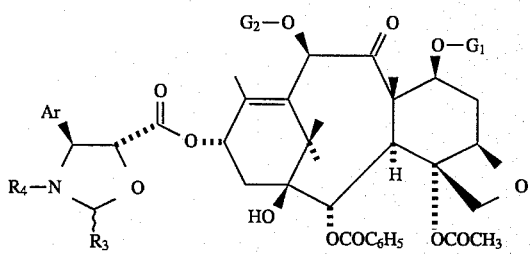

in which Ar, R₃, R₄, G₁ and G₂ are defined as above, replacing the protective groups of the hydroxyl and amino functional groups of the product obtained by hydrogen atoms to produce a product of formula:

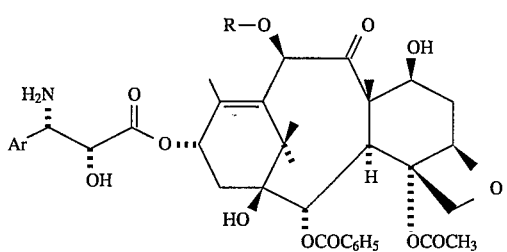

in which Ar and R are defined as above, then
  3) treating the product thus obtained with a reagent which makes it possible to introduce a substituent $R_1$ onto the amino functional group, and
  4) isolating the product obtained.

2. Process according to claim 1, wherein the esterification is carried out using an acid of formula:

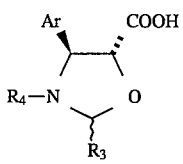

in which Ar, $R_3$ and $R_4$ are defined as in claim 1, the reaction being carried out in the presence of a condensation agent and of an activating agent in an organic solvent at a temperature between $-10°$ and $90°$ C.

3. Process according to claim 2, wherein the condensation agent is selected from imides and reactive carbonates and the activating agent is selected from aminopyridines.

4. Process according to claim 3, wherein the condensation agent is selected from dicyclohexylcarbodiimide and di-2-pyridyl ketone and the activating agent is selected from 4-dimethylaminopyridine or 4-pyrrolidinopyridine.

5. Process according to claim 2, wherein the solvent is selected from ethers, ketones, esters, nitriles, aliphatic hydrocarbons, halogenated aliphatic hydrocarbons and aromatic hydrocarbons.

6. Process according to claim 5, wherein the solvent is selected from aromatic hydrocarbons.

7. Process according to claim 1, wherein the esterification is carried out using an anhydride of formula:

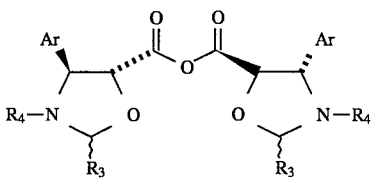

in which Ar, $R_3$ and $R_4$ are defined as in claim 1, the reaction being carried out in the presence of an activating agent in an organic solvent at a temperature between $0°$ and $90°$ C.

8. Process according to claim 7, wherein the activating agent is selected from aminopyridines.

9. Process according to claim 8, wherein the activating agent is selected from 4-dimethylaminopyridine or 4-pyrrolidinopyridine.

10. Process according to claim 7, wherein the solvent is selected from ethers, ketones, esters, nitriles, aliphatic hydrocarbons, halogenated aliphatic hydrocarbons and aromatic hydrocarbons.

11. Process according to claim 1, wherein the esterification is carried out using an activated acid of formula:

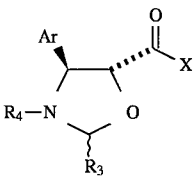

in which Ar, $R_3$ and $R_4$ are defined as above and X represents a halogen atom or an acyloxy or aroyloxy radical, optionally prepared in situ, in the presence of a base, the reaction being carried out in an organic solvent at a temperature between 10 and $80°$ C.

12. Process according to claim 11, wherein the base is selected from nitrogenous organic bases.

13. Process according to claim 12, wherein the nitrogenous organic base is selected from aliphatic tertiary amines, pyridine and aminopyridines.

14. Process according to claim 11, wherein the organic solvent is selected from ethers, ketones, esters, nitriles, aliphatic hydrocarbons, halogenated aliphatic hydrocarbons and aromatic hydrocarbons.

15. Process according to claim 14, wherein the solvent is selected from aromatic hydrocarbons.

16. Process according to claim 1, wherein replacement by hydrogen atoms of the protective groups of the hydroxyl and amino functional groups is carried out by treatment with zinc, optionally in combination with copper, in the presence of acetic acid at a temperature between $20°$ and $60°$ C.

17. Process according to claim 1, wherein replacement by hydrogen atoms of the protective groups of the hydroxyl and amino functional group is carried out using an inorganic or organic acid in solution in an aliphatic alcohol containing 1 to 3 carbon atoms or in an aliphatic ester in the presence of zinc, optionally in combination with copper.

18. Process according to claim 16, wherein $G_1$ and optionally $G_2$ represent a 2,2,2-trichloroethoxycarbonyl or 2-(2(trichloromethyl)propoxy)carbonyl radical.

19. Process according to claim 1, wherein the introduction of a substituent $R_1$ onto the amino functional group is carried out by reacting with benzoyl chloride or with a reactive derivative of formula:

$$R_2\text{—O—CO—Y}$$

in which Y represents a halogen atom or a residue —$OR_2$ or —O—CO—$R_2$ and $R_2$ is defined as in claim 1, the reaction being carried out in an organic solvent in the presence of an inorganic or organic base at a temperature between $0°$ and $50°$ C.

20. Process according to claim 19, wherein the solvent is selected from aliphatic esters and halogenated aliphatic hydrocarbons.

21. Process according to claim 19, wherein the base is sodium bicarbonate.

* * * * *

UNITED STATES PATENT AND TRADEMARK OFFICE
CERTIFICATE OF CORRECTION

PATENT NO. : 5,621,121
DATED : April 15, 1997
INVENTOR(S) : Alain COMMERÇON et al.

It is certified that error appears in the above-indentified patent and that said Letters Patent is hereby corrected as shown below:

Claim 1, column 10, line 49, delete "2)" and delete line break before "radical".

Claim 1, column 10, line 65, before "replacing", insert --2)--.

Claim 18, column 12, line 43,
"2-(2(trichloromethyl)propoxy)carbonyl" should read
--2-(2-(trichloromethyl)propoxy)carbonyl--.

Signed and Sealed this

Twelfth Day of August, 1997

Attest:

BRUCE LEHMAN

Attesting Officer   Commissioner of Patents and Trademarks